US006461825B1

(12) United States Patent
Carriere

(10) Patent No.: US 6,461,825 B1
(45) Date of Patent: Oct. 8, 2002

(54) IMMUNOMETRIC ASSAY KIT AND METHOD APPLICABLE TO WHOLE CELLS

(75) Inventor: Dominique Carriere, Castries (FR)

(73) Assignee: Sanofi (Societe Anonyme), Paris (FR)

( * ) Notice: Subject to any disclaimer, the term of this patent is extended or adjusted under 35 U.S.C. 154(b) by 0 days.

(21) Appl. No.: 07/879,110

(22) Filed: May 4, 1992

Related U.S. Application Data

(63) Continuation of application No. 07/330,172, filed on Mar. 29, 1989, now abandoned, which is a continuation-in-part of application No. 07/250,061, filed on Sep. 28, 1988, now abandoned.

(30) Foreign Application Priority Data

Sep. 30, 1987 (FR) ............................................ 87 13 537

(51) Int. Cl.[7] ...................... G01N 33/53; G01N 33/543
(52) U.S. Cl. .................... 435/7.24; 435/7.94; 435/975; 436/518
(58) Field of Search ................................. 435/7.2, 7.23, 435/7.24, 7.94, 975; 436/5.18, 526, 518

(56) References Cited

U.S. PATENT DOCUMENTS

| 4,376,110 A | * | 3/1983 | David et al. ................. 436/540 |
| 4,471,056 A | | 9/1984 | Grumet et al. .............. 436/513 |
| 4,599,304 A | | 7/1986 | Lanier et al. ................... 435/7 |
| 4,675,286 A | * | 6/1987 | Calenoff ....................... 435/30 |
| 4,677,061 A | | 6/1987 | Rose et al. .................... 435/39 |
| 4,690,890 A | * | 9/1987 | Loor et al. ................... 436/533 |
| 4,832,940 A | | 5/1989 | Ege .............................. 424/1.1 |
| 4,837,167 A | * | 6/1989 | Schoemaker et al. ....... 436/548 |
| 4,956,281 A | * | 9/1990 | Wallner et al. ............. 435/69.3 |

FOREIGN PATENT DOCUMENTS

| EP | 0 101 912 | | 3/1984 |
| EP | 0 119 736 | | 9/1984 |
| EP | 0165681 | * | 12/1985 |
| EP | 0 179 007 | | 4/1986 |
| FR | 2550799 | * | 2/1985 |
| GB | 2181840 | * | 4/1987 |
| WO | 83/02954 | | 9/1983 |
| WO | 84/03151 | | 8/1984 |
| WO | 8502685 | * | 6/1985 |
| WO | WO86/02733 | | 5/1986 |
| WO | 86/04421 | | 7/1986 |
| WO | 86/04782 | | 8/1986 |
| WO | WO86/07633 | | 12/1986 |
| WO | 87/05398 | | 9/1987 |
| WO | WO87/06620 | | 11/1987 |

OTHER PUBLICATIONS

Douillard, et al, "Enzyme–Linked Immunosorbent Assay For Screening Monoclonal Antibody Production: Use Of Intact Cells As Antigen", *Journal of Immunological Methods*, 36:309–316, (1980).

Levy, et al, "Typing Of Murine Cell–Surface Antigens By Cellular Radioimmunoassay", (1981), *Journal of Immunological Methods*, 41:333–341, (1981).

Serie, et al, "Prolongation Of Culture–Isolated Neonatal Islet Xenografts Without Immunosuppression", *Transplantation*, 36:6–11, (1983).

Walker, et al, "Some Fixation Reagents Reduce Of Abolish The Detectability Or Ia–Antigen And HLA–DR On Cells", *Journal of Immunological Methods*, 67:89–99, (1984),.

Van Riet, et al, "Pea Lectin As A Universal Cell Binding Agent For ELISA (Screening) Tests", *Journal of Immunological Methods*, 76:129–134, (1995).

Hessian, et al, "Development Of An Enzyme Immunoassay For The Quantitation Of Cellular Antigen Expression", *Journal of Immunological Methods*, 91:29–34, (1986).

Drover, et al, "Glutaraldehyde Fixation Of Target Cells to Plastic For ELISA Assays Of Monoclonal Anti–HLA Antibodies Produces Artefacts", *Journal of Immunological Methods*, 90:275–281, (1986).

Baumgarten H., "A Cell ELISA For The Quantitation Of Leukocyte Antigens Requirements For Calibration", *Journal of Immunological Methods*, 94:91–98, (1986).

Igietseme, et al, "Quantitative Measurement Of T–Lymphocyte Activation By An Enzyme–Linked Immunosorbent Assay (ELISA) Detecting Interleuken–2 Receptor Expression", *Journal of Immunological Methods*, 97:123–131.

Savion, et al, "Solid–Phase Radioimmunoassay For The Measurement Of Surface Antigens Expressed ON Intact Lymphocytes", *Journal of Immunological Methods*, 97:49–56, (1987).

Endl, et al, "A New ELISA–Based Assay For Quantitation Of Human T–Lymphocyte Subpopulations", *Journal of Immunological Methods*, 102:77–83, (1987).

Korbowiak, et al, "Determination Of Lymphocyte Subpopulations By Enzyme Immunoassay", *Journal of Immunological Methods*, 112:31–35, (1988).

Brown, et al, "Quantitative Analysis Of Melanoma–Associated Antigen p87 In Normal And Neoplastic Tissues", *Proc. Natl. Acad. Sci. USA*, 76:539–543, (1981).

Stocker et al, *Journ. Immunol. Meth.*, 26587–95, 1979.*

Hood et al, *Immunology*, 2nd Edition, Benjamin/Cummings Publishing Company, Inc., Menlo Park, CA, 1984. p.13.*

D.A. Nelson et al. in J. B. Henry (ED.), *Clinical Diagnosis And Management By Laboratory Methods*, W.B. Saunders Company, Philadelphia, 1979, p. 882.*

* cited by examiner

Primary Examiner—David Saunders
(74) Attorney, Agent, or Firm—Foley & Lardner

(57) ABSTRACT

A process and kit which permit quantitative measurement in a single analysis step of a target antigen of a whole cell. The process and kit utilize a solid support onto which is bound at least one antibody that binds to and immobilizes the subject whole cell at a surface antigenic site other than the target antigen. A second, labeled antibody specific for the target antigen is then added, and the binding is then quantitatively measured by analytical means. The process of this invention can provide rapid quantitative assay, e.g., less than one hour, of multiple samples.

8 Claims, No Drawings

IMMUNOMETRIC ASSAY KIT AND METHOD APPLICABLE TO WHOLE CELLS

This application is a continuation of application Ser. No. 07/330,172, filed Mar. 29, 1989, and now abandoned, which is a continuation-in-part of application Ser. No. 07/250,061, filed Sep. 28, 1988 and now abandoned.

The present invention relates to a kit and to an immunometric assay method using this kit for the determination of surface antigens characteristic of populations or subpopulations of cells. The immunometric assay method and the corresponding kit are also intended for the determination of the cells themselves via the determination of their surface antigens. These determinations are applicable to diagnosis.

Knowledge of the antigens or markers on the cell surface has made enormous advances with the development of lymphocyte hybridization and the discovery of monoclonal antibodies by KOEHLER and MILSTEIN (Nature, 1975, 256, 495–497). In particular, monoclonal antibodies have made it possible to reveal and analyze membrane antigens or surface markers of cells of the widest possible variety of origins. These markers (or antigens) can be of different kinds: proteins, glycoproteins or glycolipids. The characterizations sought therefore apply mainly to tissue or organ markers, to markers of states of differentiation or activation of normal cells and to the identification or typing of normal or cancerous cells. A particularly important field of application is the study of the cell lines of he mopoiesis (erythrocyte, megakaryocyte, granulocyte, monocyte, lymphocyte).

Thus, for example, monoclonal antibodies have made it possible to specify the respective surface characteristics of T and B lymphocytes. The corresponding markers, by themselves or in combination, identify stages of differentiation and functional specialization of the lymphocytes. By international convention, the surface markers of human leukocytes have been classified in differentiation groups or differentiation classes (CD) defined by the IUIS-WHO subcommittee, 1984, and described in Bulletin of the World Health Organization, 1984, 62(5), 813–815.

The identification of these markers which has been made possible by monoclonal antibodies has provided access to their structure and their biological functions. For example, the molecules of the CD4 and CD8 markers participate in leukocyte adhesion functions and are present on the surface of T lymphocytes with an auxiliary and inductive function (CD4 marker) or, respectively, with a cytotoxic and suppressive function (CD8 marker).

With this knowledge established, it has been possible to use these markers, by virtue of the antibodies which recognize them, for diagnosing and following up a variety of pathologies including, in particular, malignant hemopathies (leukemias, lymphomas, etc.) and states of dysfunction of the immune system (autoimmune diseases, congenital or acquired immune deficiencies such as AIDS, etc.) (BRETON-GORIUS and VAINCHENKER, Le Biologiste, 1987, XXI, no. 167, 63–70; SHAW, Immunology Today, 1987, 8(1), 1–3).

Monoclonal antibodies are now irreplaceable tools of clinical biology applied to cell analyses.

Cell counting methods exist which use the marking of their surface antigens, but these methods are often lengthy, laborious and difficult to carry out and their results are sometimes random.

The known methods used for measuring the normal or modified expression of antigens on the surface of the cell can be separated into two groups. In the first group, the antigens are measured with the aid of complex and specialized laboratory equipment based on flow cytometry (see, in particular, PONCELET et al., J. Immunol. Methods, 1985, 85, 65–74) or quantitative microscopy techniques (POULTER et al., J. Immunol. Methods, 1987, 98, 227–234). These methods for the evaluation of cell antigens are based on the measurement of signals provided by anticell antibodies coupled directly or indirectly to a reagent labeled with fluorescent substances (or fluorochromes) such as fluorescein isothiocyanate or rhodamine isothiocyanate, or with enzymes such as peroxidase or alkaline phosphatase. The use of these fluorescent or enzyme reagents in association with appropriate washing steps then leads to the appearance of fluorescences or colorations which are strictly limited to the cell membranes and do not diffuse into the surrounding medium. Common use of these methods in the laboratory is still restricted by the need for specialized and expensive equipment (a fluorescence microscope which may or may not be associated with an image analyzer, a cryostat and a flow cytometer). Moreover, the analysis and interpretation of th immunolabeling of cells by these processes demand the competence of a specialist in cytology.

A second group of methods for the measurement of antigens is based on the quantitative evaluation of the markers of the overall cell population. These methods make it possible to measure antigens either by direct labeling or by indirect labeling, the latter most frequently being carried out in two, three or four steps. In all cases, the reagent employed in the last labeling step carries a probe which is either of isotopic character, for example iodine 125, for a determination of the radioimmunometric type (BROW et al.,J. Immunol. Methods, 1979, 31, 201; STOCKER and HEUSSER, J. Immunol. Methods, 1979, 26, 87–95), or an enzyme for a determination of the enzyme immunometric type, most frequently peroxidase, alkaline phosphatase or beta-galactosidase (VAN LEUVEN et al., J. Immunol. Methods, 1978, 23, 109–116; MORRIS, Transplantation, 1983, 36(6), 719; BAUMGARTEN, J. Immunol. Methods, 1986, 94, 91–98).

The methods in this last group are rather inconvenient, laborious and risky to apply because of the need to ash and centrifuge the cell material many times; it is sometimes necessary to take a sample of the colored medium resulting from the enzyme reaction in order to carry out the final spectrophoto-metric measurement; finally, chemical fixation of the cells, which is used in most cases, causes the irreversible destruction of certain antigens which are particularly sensitive to the customary chemical binding agents such as glutaraldehyde or methanol (DROVER et al., J. Immunol. Methods, 1986, 90, 275–281).

It is known in the literature that an antigen carrying several antigenic determinants, i.e. several epitopes, can be determined by fixing this antigen via one of its epitopes using an antibody immobilized on a solid support, and by binding, to another epitope of the antigen, another antibody carrying an enzyme or radioisotopic marker enabling the determination to be carried out.

This kind of technique, which is often referred to as the sandwich technique, is described especially in French Patent 2 487 983, French Patent 2 500 166 and European Patent Application 119 736. None of these documents describes the application of this technique to whole cells, even though the word "cell" is sometimes included in the list of antigens to which the process applies.

In the above patents, the various antigens forming the subjects of the Examples described are in all cases solely protein molecules soluble in water and physiological liquids, such as tumoral markers, enzymes or hormones in the bloodstream. On the other hand, it is clear that a cell is not a molecule and differs therefrom at least by being considerably larger and by the fact that it is not soluble in physiological media. Thus,the sandwich technique has so far never been applied to whole cells.

Furthermore, the immunocapture of cells on a solid support is described in International Patent Application 86/02091, in which the object is to remove undesirable cells from samples of bone marrow intended for transplantations. In the said patent application, capture of the cells is effected on floating microbeads and requires that the antibody used be bound to the solid support by a complex macromolecular structure, called a network-relay, which is capable of ensuring a preferential orientation of the antibody relative to that of the corresponding cell antigen. The said patent application gives no indication of an application of the technique to the quantitative determination of an antigen.

The immunocapture of cells is also described in International Patent Application 84/03151 for an analytical application. In the said patent application, the object is to identify the tissue groups to which the examined cells belong (this operation generally being called HLA typing). The cells are captured by means of antibodies arranged according to a particular geometry on very specialized supports (microscope cover glasses). The results are obtained simply by visual observation of the support and produce "all or nothing" responses. Thus the cell immunocapture systems described hitherto do not lead to analytical applications permitting the quantitative determination of an antigen expressed at the membrane of certain cells. Furthermore, all these systems may lack specificity because they are based on recognition of the cells by a single antibody.

The method of determination forming the subject of the present invention has considerable advantages compared with all the techniques known and used in the prior art, since it permits the quantitative measurement of any antigen of a cell population in a single analysis step. This determination is carried out on cells which have not undergone any chemical or physical intervention and which are in their state of physiological integrity. Furthermore, the method of determination according to the invention has the characteristics of very high specificity which are inherent in the double immunological recognition systems involving 2 different antibodies specific for 2 different antigens carried by the same cell. This method is simple, rapid and reproducible. It is totally suitable for the analysis of a large number of samples, which enables it to be used for diagnostic purposes in clinical biology laboratories handling these large numbers.

The present invention thus relates to a kit for the determination of at least one surface antigen characteristic of a cell population or subpopulation, which comprises the following components:

a) a solid support to which one or more monoclonal antibodies are fixed by covalent bonding or physical adsorption, the said monoclonal antibodies being directed against surface antigens of the cell population examined, other than the said characteristic antigen, and being intended to immobilize, on the support, the cells which include those of the subpopulation carrying the antigen to be determined;

b) at least one solution comprising a monoclonal antibody specific for the said antigen characteristic of the cell population or subpopulation carrying the antigen to be determined, which is labeled with a radioisotopic probe or an enzyme probe; and c) in the case of monoclonal antibodies labeled with an enzyme probe, a developer for the enzyme, namely one or more solutions containing the substrate for the enzyme and, if necessary, one or more reagents necessary for developing the activity of the enzyme.

The term "cell" as used in the present specification and in the claims which follow includes human cells, animal cells, the cells of protozoans and the cells of microorganisms (bacteria or fungi). As regards blood cells, the present invention includes the nucleate formed elements, such as the leukocytes, and the a nucleate formed elements, such as the erythrocytes or platelets.

The method of determination according to the invention applies to whole cells, i.e. non-lyzed cells.

These cells have not undergone any physical or chemical intervention and they are used in a state of complete physiological integrity. This situation constitutes the best guarantee of integrity of the membrane markers chosen as targets for determination.

As the solid support it is possible to use any device suitable for the handling of cell suspensions, and preferably tubes, particulate magnetic supports or rigid or flexible microtiter plates made of polyethylene, polystyrene, polyvinyl chloride or nitrocellulose, which contain microwells. The monoclonal antibodies intended for immobilization of the cells can be fixed to the solid supports either by covalent chemical bonding or by physical adsorption according to conventional methods such as those disclosed by STOCKER and HEUSSER J. Immunol. methods, 1979, vol. 26, p. 87–95. Advantageously, the support is saturated with a protein beforehand.

According to the invention, the monoclonal antibody or antibodies fixed to the solid support must permit the immunocapture of the cell population which includes the cell population or populations carrying the antigens to be determined. When this population consists of human cells, the preferred monoclonal antibodies for immunocapture are the anti-class I HLA antibodies which are specific for the common part of the HLA-A, -B and -C antigens present on the leukocytes and numerous other cell lines of the organism. Of these antibodies, the one called S-class I, marketed by BIOSYS, is particularly preferred.

In other cases where the cells examined are human cells and in all cases where these cells are not human cells, monoclonal antibodies appropriate to the type of cells examined can also be used for the immunocapture according to the invention.

The expression "a monoclonal antibody labeled with a radioisotopic probe" means that the monoclonal antibody carries, either on a component inherent in its structure, for example the constituent tyrosine residues, or on an appropriate radical which has been attached thereto, a radioactive isotope which enables it to be determined by counting the radioactivity associated therewith.

The expression "a monoclonal antibody labeled with an enzyme probe" means that the monoclonal antibody is coupled to an enzyme which, when associated with the use of appropriate reagents, permits quantitative measurement of this monoclonal antibody.

The substrate and the reagents are chosen so that the final product of the reaction or reaction sequence caused by the enzyme, involving these substances, is:

either a colored or fluorescent substance which diffuses into the liquid medium surrounding the cells and which is the object of the final spectrophoto-metric or, respectively, fluorimetric measurement, or an insoluble colored substance which deposits on the cells and the walls to which they are fixed, and which can be the object either of photometric measurement by reflection or of visual evaluation, if appropriate against a range of standard shades.

As an additional component, the assay kit can contain a buffer solution intended for washing the solid support after immobilization and labeling of the cells with the antibody or antibodies carrying the chosen probe.

As additional components, the assay kit can also contain the samples necessary for standardization and quality control of the determination.

The present invention further relates to a process for the immunometric assay of the surface antigens of a cell population or subpopulation, the said process comprising:

a single step for the specific immobilization or immunocapture of a cell population on the solid support using one or more monoclonal antibodies fixed to the said support beforehand by covalent bonding or by physical adsorption and capable of recognizing an antigen present on the surface of the cells, other than the antigen to be determined, and, simultaneously, the direct labeling of the surface antigen to be determined, belonging to the immobilized cell population or to one of its subpopulations, with a monoclonal antibody specific for this antigen to be determined, the said monoclonal antibody carrying a radioisotopic or, alternately, enzyme probe;

an incubation period to allow the simultaneous immunocapture and labeling to take place;

the washing of the solid support to remove the nonimmobilized undesirable cells and the excess of monoclonal antibody carrying the radioisotopic or enzyme probe; and the actual determination of the antigen to be determined in the labeled cell population or subpopulation by counting the fixed radioactivity or, alternately, after treatment of the medium with the substrate for the enzyme and, if necessary, one or more appropriate auxiliary reagents, by photometric measurement by transmission or reflection, or measurement of the fluorescence emission.

The assay kit and the immunometric assay process according to the invention are preferably applied to the determination of the surface antigens of the formed elements of human blood, especially the leukocytes and more particularly the lymphocytes, the T lymphocytes, the T4 lymphocytes, the T8 lymphocytes and the B lymphocytes, as well as the granulocytes, the monocytes and the blood platelets.

Another preferred application is the determination of the surface antigens of pathogenic micro-organisms, for example *Candida albicans*.

The assay kit and the immunometric assay process according to the invention are also particularly useful for the determination of the surface antigens of tumoral cells, especially those of cancers of the urinary system and those of malignant hemopathies.

The assay kit and the immunometric assay process according to the invention make it possible to measure signals (absorbed or emitted light or radioactivity) which depend both on the number of cells present in the cell population examined and on the density of the antigen measured on the surface of these cells. Measurement of these signals permits quantitative evaluation of the total number of molecules of this antigen which are carried by the cell population or subpopulation examined, whether this antigen has a structural or functional role.

For example, in the case of the leukocyte markers of particular importance in hematology, it is known that, in the majority of situations in healthy subjects, the mean value of the antigen density does not vary substantially between samples for one and the same cell population, so there is a good correlation between the cytological count of the cells carrying the antigen in question and the signal measured according to the invention, which is proportional to the total number of antigen molecules present in the sample examined. Conversely, in some pathological states, the density of the surface antigens may vary for one and the same cell population without a notable variation in the number or proportion of the positive cells. Such pathological immunometric assay process according to the invention or by using the kit of the present invention than they would be if a kit of the present invention than they would be if a conventional cytological counting procedure were used.

Another application of the invention becomes apparent if a microtiter plate is chosen as the solid support. The assay kit and the immunometric assay process according to the invention can then advantageously be used for the determination, on a single plate, of a series of surface antigens characteristic of various subpopulations making up the cell population examined.

For this application, it is possible on the one hand to take ready-to-use microtiter plates to which one or more monoclonal antibodies capable of retaining all the cells of the population examined have been fixed beforehand, and on the other hand to have a series of monoclonal antibodies coupled to an appropriate probe and each specific for an antigen characteristic of one of the subpopulations to be evaluated. Thus, in a single manipulation and on one and the same support, it is possible to carry out the quantitative determination of all the antigens necessary for characterization of the chosen subpopulations.

This application of the present invention is illustrated by the characterization of the antigenic equipment of cells of interest in clinical biology. A first case is represented by the determination of the tissue groups characterizing a given individual, which is conventionally known as HLA typing.

A second case is represented by the typing of tumoral cells, in particular for patients afflicted by malignant hemopathies such as leukemias or lymphomas. This diagnostic examination, which is practiced systematically, consists in characterizing the type and origin of the patient's tumoral cells by the presence or absence on these cells of a series of suitably chosen surface antigens.

Use of the kit according to the invention, which contains a microtiter plate on which one or more monoclonal antibodies capable of fixing all the cells of the population examined have been fixed beforehand, and solutions of different monoclonal antibodies labeled with an enzyme or radioisotopic probe and each specific for an antigen present on the tumoral cells, permits identification and quantitative evaluation of the antigens characteristic of the patient's tumoral cell population and thus makes it possible to associate them with one of the major groups of clinically characterized cancers, especially malignant hemopathies. Application of the process according to the invention thus makes it possible to carry out the qualitative and quantitative examination of the antigenic phenotyope of tumoral cells rapidly and on a single support.

A case which may be mentioned as an illustration of another application of the invention is that of the human T lymphocytes, for which there are in particular subpopulations of cells: the lymphocytes characterized by the presence of the CD4 marker, which will be called positive T4 lymphocytes or, more simply, T4 lymphocytes, and the lymphocytes characterized by the presence of the CD8 marker, which will be called positive T8 lymphocytes (or T8 lymphocytes).

Measurement of the numerical ratio T4/T8 is of great diagnostic interest in clinical biology. In fact, it is known that modifications of the T4/T8 ratio appear in various complaints of the immune system, such as dysimmune diseases, chronic infectious diseases, viral infections and, in particular, HIV complaints (AIDS virus).

The assay kit and the immunometric assay process according to the invention can be used for the determination of antigens universally characteristic of the T lymphocyte population and/or antigens characteristic of the T4 and T8 lymphocyte subpopulations. In this case, the T lymphocytes of the sample examined are specifically immobilized on a solid support and, simultaneously, the surface antigens of the T4 lymphocytes are labeled directly with an anti-CD4 monoclonal antibody carrying a radioisotopic or enzyme probe; in the same way, the surface antigens of the T8 lymphocytes are labeled directly with an anti-CD8 monoclonal antibody carrying an appropriate probe.

The total T lymphocytes are preferably determined using an anti-CD7 monoclonal antibody (also called anti-T2 monoclonal antibody) carrying an appropriate probe.

Specific immobilization of the T lymphocytes of the sample is preferably carried out using one or more monoclonal antibodies which are capable, by themselves or in combination, of recognizing all the T cells of the sample, this being the case of the anti-common leukocyte (or anti-CD45) antibodies or antibodies which recognize the whole of the T population (called "pan-T" antibodies), such as the anti-CD2 (or anti-T11), anti-CD5 (or anti-T1) or anti-CD7 (or anti-T2) antibodies or other pan-T anti-bodies which have not yet been assigned to a differentiation class according to the WHO criteria.

The immunometric assay method of the invention can advantageously be used for the determination of antigens characteristic of the population of T lymphocytes and T4 and T8 lymphocytes on several parts of the same solid support. Measurement of the signals by radioactivity counting, photometric measurement by transmission or reflection or fluorescence measurement enables the numerical ratio CD4/CD8 to be calculated easily and directly.

In the same way, it is possible to determine, on one and the same solid support, the subpopulations called T lymphocytes and B lymphocytes which make up the whole of the lymphocyte line.

For example, a monoclonal antibody or a mixture of monoclonal antibodies specific for all the surface antigens of the T cells can be fixed by adsorption to the walls of the microwells. These monoclonal anti-bodies will enable the whole population of T cells of the sample examined to be immobilized in the microwells at a later stage. The plates prepared in this way can be lyophilized and stored, preferably at 4° C. This step can be carried out on the industrial scale and it will thus be possible to have ready-to-use plates for the assay kits which can be applied either to the total T lymphocytes or to any subpopulation of T lymphocytes.

The samples containing the cells to be determined, which originate from the blood or from any appropriate biological liquid—normal or pathological—can be used as such or after preparation, especially by density gradient centrifugation according to the methods already known, and in particular in a high-density medium such as, for example, FICOLL-PAQUE marketed by Pharmacia. To determine the blood lymphocytes, the blood sample to be determined can also be treated with a so-called lysis buffer solution, which lyzes the erythrocytes.

It will be noted that particulate magnetic supports, notably magnetic beads are particularly appropriate to carry out the assay of a cell population or subpopulation contained in a biological liquid, without a previous preparation of this cell population or subpopulation from said biological liquid. For example, by using particulate magnetic supports, it is possible, according to the process of the invention to directly assay the formed elements of human blood from the complete blood or the urines.

Aliquots of the appropriate cell suspension are brought into contact with the solid support, for example in the microwells of a microtiter plate prepared beforehand, at the same time as the solution forming part of the assay kit, which contains the monoclonal antibody specific for the target cell population and carrying an appropriate probe, i.e. a radioisotopic or enzyme tracer. Thus a radioisotopic probe can be prepared for example by labeling the monoclonal antibody with iodine 125 or iodine 131, for example in the presence of chloramine T, by a known process (F. C. GREENWOOD, W. M. HUNTFR et al., Biochem. J., 1963, 89, 114); alternately, an enzyme probe can be prepared by conjugating the monoclonal antibody with an enzyme such as alkaline phosphatase, peroxidase, beta-galac-tosidase or acetylcholinesterase, by a described method (see, for example, M. O'SULLIVAN, Methods in Enzymology, 1981, 73, 147) or by a method based thereon. In some cases, in order to avoid certain disadvantages associated with the handling of radioactive substances and the limited shelf life of the reagents, enzymes will be used in preference to radioisotopic probes.

The incubation period, i.e. the time required for immobilization and simultaneous labeling of the cells, is preferably less than or equal to 1 hour. During this time, the solid support can be centrifuged, if necessary, in order to improve the immobilization of the cells. The solid support, for example the microtiter plate, is then washed to remove the non-fixed cells and at the same time the excess of monoclonal antibody carrying an enzyme or radioisotopic probe.

When a radioisotopic probe is used, for example iodine 125, the radioactivity associated with the cells is counted in a gamma counter according to any appropriate procedure and, for example, after solubilization of the cells with an alkaline solution (for example a sodium hydroxide solution) and recovery of the solution containing the radioactivity by means of an absorbent buffer.

When an enzyme probe is used on the monoclonal antibody, the appearance of a colored or fluorescent product is brought about by adding, to the solid support to which the cell population carrying the antigen to be determined has been fixed, a solution containing the substrate for the enzyme and one or more auxiliary reagents such that the reaction product which is finally obtained is either a colored product soluble in the medium, or an insoluble colored product, or a soluble fluorescent product, as explained earlier. The light signal coming from the samples treated in this way is then measured with the equipment appropriate to each case, i.e. a transmission or reflection photometer or, respectively, a fluorimeter. When the solid support is a microtiter plate, the light signal can be read sequentially in all the wells of one and the same plate by means of automated readers commonly used in biology laboratories, such as the Titertek plate reader or the Fluoroscan plate reader for the spectrophotometric or, respectively, fluorometric readings.

When alkaline phosphatase is used as the enzyme probe, this enzyme is coupled to the monoclonal antibody according to the method proposed by Boehringer Mannheim—Biochemica. The preferred substrates for this enzyme are paranitrophenyl phosphate for a spectrophotometric final reading, 4-methylumbelliferyl phosphate for a fluotimetric reading or 5-bromo-4-chloroindol-3-yl phosphate for obtaining an insoluble colored reaction product. Likewise, beta-galactosidase can be used as the enzyme probe, in which case the preferred substrates will be orthonitrophenyl beta-D-galactopyranoside or 4-methylumbelliferyl beta-D-galactopyranoside.

The monoclonal antibodies can preferably be coupled to peroxidase. In this case, the coupling process is derived from that described by M. B. WILSON and P. K. NAKANE in Immunofluorescence and Related Staining Techniques, edited by W. Knapp, K. Kolubar and G. Wicks, Elsevier/North Holland, Amsterdam, 1978, p. 215–224. The modifications which have been introduced by comparison with the initial protocol for preparation of the enzyme conjugate concern the following points:

the molar ratio peroxidase/antibody is equal to 3 as opposed to 2 in the protocol, and oxidation of the carbohydrate units of the peroxidase is less harsh due to a 33% reduction in the proposed concentration of sodium periodate.

The reagents used to develop the peroxidase conjugated with the monoclonal antibodies contain hydrogen peroxide, which is the substrate for the enzyme, and an appropriate chromogen, for example orthophenylene-diamine or 2,2'-azino-bis(3-ethylbenzothiazoline-6-sulfonic) acid, or ABTS, to give a final reaction product which is colored and soluble in the medium, or else 3,3'-diaminobenzidine, 3-amino-9-ethylcarbazole or 4-chloro-alpha-naphthol to give an insoluble final reaction product, or else parahydroxyphenyl-propionic acid to give a fluorescent reaction product which is soluble in the medium.

In a preferred form, the kit according to the invention for the determination of antigens characteristic of the T, T4 and T8 lymphocytes comprises:

a) a microtiter plate in whose wells one or more monoclonal antibodies directed against T lymphocytes have been fixed, b1) a solution containing at least one peroxidase-labeled monoclonal antibody directed against T lymphocytes, b2) a solution containing at least one eroxidase-labeled monoclonal antibody directed gainst CD4 antigen, b3) a solution containing at least one peroxidase-labeled monoclonal antibody directed against CD8 antigen, c1) a solution containing hydrogen peroxide, which is the substrate for the enzyme, in an appropriate buffer, and c2) a solution containing the chromogen used to develop the expression of the enzyme's activity.

Another preferred embodiment of the invention is the use of monoclonal antibodies coupled to acetyl-cholinesterase.

The acetylcholinesterase is preferably coupled to the antibody using a process derived from that described in French Patent no. 2 550 799 or a process which schematically involves the preparation of fragments of the antibody by a known technique, the modification of the enzyme by reaction with an appropriate hetero-bifunctional agent and, finally, the coupling of the resulting products. Other known processes for constructing immunoenzyme conjugates can also be used in this case.

Development of the enzyme activity specifically associated with the cell antigen recognized by the acetylcholinesterase conjugate is preferably carried out by the known technique which employs acetylthiocholine as the substrate for the enzyme and Ellman's reagent, or 5,5'-dithio-2-nitrobenzoic acid, as the chromogen, in accordance with any variant suitable for the case under examination, for example the one described by Pradelles et al., Anal. Chem.,57 (1985) 1170–1173.

The chromogens cited are used as such or in the form of water-soluble salts.

The results of the determination of antigens according to the invention can be expressed in any form appropriate to the examination carried out. More particularly, these results can be expressed either as the total number of molecules of a particular antigen (for example the CD4 antigen) present in a given volume of the sample examined (for example per microliter of blood), or as the ratio of the number of molecules of one antigen to the number of molecules of another antigen in the sample examined (for example the ratio of the CD4 antigens to the CD8 antigens—or CD4/CD8 ratio—in the blood sample examined).

The number of molecules of a particular antigen in the sample examined will preferably be determined using a standard range consisting of appropriate cells or cell preparations carrying the antigen to be determined, which will have been calibrated beforehand by a known reference method. These standards will preferably consist either of cells identical in their origin to the cells which are to form the subject of the determination, or of cells of established cell lines carrying the desired antigen, or of preparations, for example membrane preparations, originating from these cells.

These standards are then treated in exactly the same way as the samples to be examined. The resulting signals are used to build up a standard range against which the signals measured with the samples to be examined are compared. The subsequent calculations are conventional.

To determine the ratio of the numbers of molecules of two antigens in the sample to be examined, it is possible to use the standard system described above and finally to calculate the desired ratio. A simpler possibility in many cases is directly to calculate the ratio of the specific signals obtained with each of the desired antigens and to correct it, if necessary, by means of known factors such as the ratio of the dimensions of the samples used; this gives the desired ratio directly.

The immunometric assay method according to the invention is simple, rapid and reproducible. Its use is totally suitable for the analysis of a large number of samples. For an understanding of its advantages compared with the other methods described, the various steps of the method according to the invention should be analyzed.

The immobilization of the cells on the solid support is the phase of the determination which usually presents the most difficulties or which is the most critical to carry out. The means often used is chemical fixation of the cells with glutaraldehyde or methanol in cups which may or may not have been treated with poly-L-lysine (F. VAN LEUVEN et al., J. Immunol. Methods, 1978, 23, 109). However, chemical fixations performed in this way can reduce or even suppress the desired specific detection or conversely can induce the false-positive labeling of cells, which is a very serious disadvantage (DROVER and MARSHALL, J. Immunol. Methods, 1986, 90, 275–281).

Furthermore, the chemical fixation process has to be carried out in several steps: centrifugation of the cells, preparation of the fixative mixture, fixation and then washing of the fixed cells several times.

Drying of the cells at 37° C., optionally followed by fixation with methanol in the microwells, has also been proposed (BAUMGARTEN, J. Immunol. Methods, 1986, 94, 91–98). Actually, in addition to the fact that it can degrade certain fragile antigens, drying of the cells at 37° C. renders the pericellular plasmic membrane permeable, thereby facilitating the immunolabeling of intracyto-plasmic antigens as well as labeling of the surface antigens, which leads to troublesome backgrounds or to false-positive results when it is desired to restrict a measurement to the surface antigens.

Furthermore, the reproducibility of this process is doubtful; in fact, the settling of the cells in the assay microwells and the drying of the cells can vary between experiments. Finally, this determination is long to perform because the cell drying step alone takes more than 2 hours.

The immobilization of lymphocytic populations has also been achieved by the use of polyclonal antibodies adsorbed in microwells (STOCKER and HEUSSER, J. Immunol. Methods, 1979, 26, 87–95). Apart from permitting the immobilization of cells foreign to the single population which it is desired to analyze, polyclonal antibodies also have the disadvantage of reacting with the antigens which are to be measured by means of the labeled antibody, leading to a corresponding reduction in the signal which is finally measured.

The use of highly specific and related monoclonal antibodies adsorbed on or fixed to the solid support, and especially in the assay wells, permits exclusive capture of the desired cells, the other non-retained cell populations being removed in the course of the washing operations carried out on completion of the labeling of the antigens to be determined. Furthermore, no chemical or physical agent modifies the characteristics of the antigens in this step because the various operations for chemical or physical fixation of the cells to the support are omitted.

Thus, according to the present invention, it has been found that the immobilization of cells by monoclonal antibodies is a process which makes it possible to simplify the step for immobilizing the cells carrying the antigen to be determined, while at the same time making the results more reliable.

Immunometric assays applied to cell populations are generally carried out by labeling the cells according to an indirect method in 2 or 3 successive steps, the probe which provides the specific signal being fixed to the cells during the last step of the labeling process. In the labeling of cells in two steps, the main reagents involved use anti-immunoglobulin (anti-Ig) antibodies coupled to beta-galactosidase (COBBOLD et al., J. Immunol. Methods, 1971, 44, 125–133) or to alkaline phosphatase (HESSIAN, J. Immunol. Methods, 1986, 91, 29–34) or labeled with iodine 125 (SAVION, J. Immunol. Methods, 1987, 97, 49–56). The technique of labeling with the peroxidase-antiperoxidase reagent is carried out in 3 steps (VAN LEUVEN, 1978).

Another process, also in 3 steps, uses a monoclonal antibody specific for the antigenic marker to be analyzed, then anti-mouse Ig antibodies carrying biotin, and finally a streptavidine-peroxidase conjugate (BAUMGARTEN, 1986) or streptavidine-alkaline phosphatase conjugate (IGIETSEME et al., J. Immunol. Methods, 1987, 97, 123–131).

The process according to the invention, which comprises the simultaneous use, in a single step, of a procedure for immunocapture of whole cells without physical or chemical intervention on the cells, and of the labeling of all or some of these cells with one or more monoclonal antibodies directly carrying a radioiso-topic or enzyme probe, is the first process to permit the Quantitative determination of chosen membrane antigens on the cells themselves.

According to the invention, the direct labeling of immunologically immobilized cells permits:
simplification of the method of determination by elimination of the intermediate manipulations repeated between the successive steps of the labeling process in the case of indirect labeling: centrifugation of the cells several times, removal of the labeling reagents and resuspension;

a saving of reagents;

an improved reliability through a reduction in the number of steps and manipulations;

a time saving; and the possibility of treating large numbers of samples at the same time, exclusively with the use of conventional equipment and apparatuses.

The incubation period for immobilization of the cell population and simultaneous direct labeling of the antigens of the cell subpopulation to be determined is short. It is less than or equal to 1 hour in the case of the determination of T lymphocytes and subpopulations of T4 and T8 lymphocytes.

After the solid support has been washed, the actual determination is carried out by using conventional apparatuses to observe a signal which is precise and simple to measure: radioactivity or light absorption or emission.

Thus, overall, the process according to the invention has numerous advantages: it is rapid, reliable, economic and simple.

The process according to the invention makes it possible to determine surface antigens of a cell population over a wide range of cell concentrations.

The sensitivity of the method in respect of the number of cells depends on the antigen density of the cell population determined. For each antigen it is possible, if desired, to define the minimum molar concentration of antigen which can be measured by the process according to the invention.

Thus, for example, when the chosen solid support is a microtiter plate and the cells examined are human lymphocytes, it has been observed that significant measurements are obtained when the number of cells analyzed is between a few hundred and about 200 000 per 200 $\mu$l microwell, the lower limit being imposed by the density of the measured antigen on the cells examined and the sensitivity of the chosen detection technique, while the upper limit depends essentially on the size and geometry of the solid support. The same applies in the case where the solid support consists of tubes.

It has been verified that the signals recorded (radioactivity count or photometric measurements) make it possible to obtain satisfactory uniform calibration curves as a function of the number of cells used, under the customary handling conditions.

Furthermore, the sensitivity of the method can be improved, if necessary, by the simultaneous fixation, to one and the same surface antigen, of several different monoclonal antibodies specific for several different epitopes of the same antigen. This has been verified by determination of the CD4 antigens on cells of the Ichikawa line (human T line), where the OKT4 and ST4 antibodies labeled with iodine 125 were used simultaneously. The measured signal increased by about 50% relative to the signals obtained with each of the anti-CD4 antibodies used by itself.

In the Examples which follow, the following terms or their abbreviations will be used indiscriminately:

| | |
|---|---|
| BSA | : bovine serum albumin |
| PBS | : phosphate buffered saline of pH 7.4 |
| POD | : peroxidase |
| IgG | : immunoglobulin G |
| IgM | : immunoglobulin M |

-continued

| | |
|---|---|
| anti-T IgG or anti-T | : antibody directed against T lymphocytes |
| anti-CD4 IgG or anti-CD4 | : antibody directed against CD4 antigen |
| anti-CD8 IgG or anti-CD8 | : antibody directed against CD8 antigen |
| cpm | : counts per minute |
| dpm | : disintegrations per minute |

EXAMPLE 1

Enzyme immunometric assay of the molecular concentration of the CD4 and CD8 antigens in samples of human blood, in which the antibodies are labeled with peroxidase A) Preparation of the Assay Kit a) Preparation of the plate The plate used is a plastic microtiter plate containing 96 microwells, marketed by NUNC (reference 64394). Each microwell receives 200 µl of a solution containing the purified anti-CD2 monoclonal antibody (called ST11) used to immobilize the total T lymphocytes, i.e. to effect their immunocapture. This antibody, marketed by BIOSYS, Compiegne, France, under the reference ST11, is used at a concentration of 10 µg/ml in a phosphate buffered saline (PBS) of pH 7.4. The adsorption of the monoclonal antibody is effected at 4° C. for 12 hours. The excess antibody is removed by turning the plate over.

A solution containing 0.1% of gelatin and 0.5% of BSA in a phosphate buffered saline is prepared. 250 ° C. of this solution are introduced into each microwell so as to saturate the surface of the wells with protein, which takes 1 hour at 37° C.; the plates are washed 3 times with phosphate buffered saline. The plates prepared in this way are lyophilized and stored at 4° C. in a sealed plastic sachet.

b) Preparation of the solution of monoclonal antibody-peroxidase conjugate

The peroxidase (POD) marketed by Boehringer Mannheim Biochemica (reference 814 393) is used.

The process for coupling the antibody to the peroxidase is the one described by M. B. WILSON and P. K. NAKANE in Immunofluorescence and Related Techniques (edited by W. KNAPP, K. KOLUBAR and G. WICK, 1978, Elsevier/North Holland, Amsterdam—p. 215–224), except that the oxidation of the peroxidase is carried out using 1.5 mg of POD in 0.36 ml of distilled water and that 50 µl of a 0.2 M solution of sodium periodate are added. The resulting product is coupled to 2 mg of anti-CD4 IgG contained in 500 µl of carbonate buffer. After treatment with sodium borohydride and dialysis against PBS, the IgG-POD conjugate is sterilized by filtration on a 0.22 µm membrane and kept under sterile conditions at a concentration of 0.5 mg of IgG per ml, at 4° C., in glass tubes. The reagent is stable for at least 1 year.

The anti-CD8 IgG-POD conjugate is prepared in the same way. IgM-POD conjugates can be prepared by the same method.

c) Preparation of the developing reagent

The developing reagent is obtained in the following manner: A 0.1 M citrate buffer is prepared by dissolving citric acid monohydrate in water at a concentration of 2.1% and adjusting the pH to 5 by the addition of 7 N sodium hydroxide solution. 30 mg of orthophenylenediamine dihydrochloride are then added to 20 ml of the citrate buffer obtained, after which 40 µl of 30% hydrogen peroxide (substrate for the enzyme) are added, at the last moment, per 20 ml of citrate buffer containing orthophenylenediamine.

B) Immunometric Assay Process a) Separation of the cells 2 ml are taken from the blood sample to be determined. This is mixed with 2 ml of phosphate buffered saline and the resulting mixture is deposited on top of 3 ml of FICOLL-PAQUE (marketed by Pharmacia). On centrifugation at 400×g for 30 minutes at room temperature, a suspension ring containing the mononucleate cells is formed. The whole of this suspension is recovered in a volume of 1 ml and 6×100 µl of the resulting suspension are distributed into 6 microwells of the preprepared plate.

b) Incubation of the cells

The previously obtained POD-antibody conjugate is diluted 100-fold with PBS containing 1% of a protein substance such as BSA or skimmed milk powder, and 100 µl of this solution are deposited in each microwell as follows:

2 microwells are each filled with 100 µl of the solution of the POD-anti-CD4 conjugate;

2 microwells are each filled with 100 µl of the solution of the POD-anti-CD8 conjugate; and 2 control microwells are each filled with 100 µl of a 1% solution of protein substance (reaction blank).

To improve the fixation of the cells to the support, the plate is centrifuged for 3 minutes at 150×g after a wait of 1 hour at room temperature.

c) Development of the fixed enzyme and measurement

The microwells are emptied by turning the plate over. They are washed 4 times with 200 µl of PBS. 200 µl of the developing reagent, prepared for immediate use, are added to each well. Incubation is carried out for 20 minutes at room temperature in subdued light. The optical density is measured on a spectrophotometer at 492 nm (type 310 C Titertek Multiskan apparatus—Flow Laboratories).

d) Standardization and expression of the results

To standardize these experiments, a preparation of total human lymphocytes was used which had been calibrated beforehand in respect of CD4 and CD8 antigens by the cytofluorometric technique of PONCFLET et al. (J. Immunol. Methods, 1985, 85, 65–74). Known aliquots of this reference preparation were used to make up the 2 standard ranges relating to the CD4 antigen and CD8 antigen respectively, against which the numbers of antigens corresponding to each sample are calculated.

By way of indication, Table 1 below shows, for 20 samples of human blood taken from healthy donors, the optical density values obtained, the corresponding numbers of molecules of CD4 and CD8 antigens and the resulting ratios of these numbers of antigens (CD4/CD8 ratios).

TABLE 1

| | CD4 antigen | | CD8 antigen | | |
|---|---|---|---|---|---|
| Donor number | Optical density | Number of antigen molecules (in millions) per µl of blood | Optical density | Number of antigen molecules (in millions) per µl of blood | Molar ratio CD4/CD8 |
| 1 | 0.64 | 23 | 1.29 | 92 | 0.25 |
| 2 | 0.71 | 27 | 0.75 | 37 | 0.73 |
| 3 | 0.82 | 32 | 1.10 | 81 | 0.39 |
| 4 | 0.49 | 17 | 0.55 | 23 | 0.74 |
| 5 | 0.74 | 29 | 0.89 | 52 | 0.56 |
| 6 | 0.88 | 38 | 0.92 | 55 | 0.69 |
| 7 | 0.74 | 29 | 0.72 | 36 | 0.80 |
| 8 | 0.75 | 29 | 0.69 | 33 | 0.88 |
| 9 | 0.48 | 16 | 0.80 | 41 | 0.39 |
| 10 | 1.00 | 50 | 1.08 | 80 | 0.62 |
| 11 | 0.61 | 22 | 0.69 | 33 | 0.67 |

TABLE 1-continued

|  | CD4 antigen | | CD8 antigen | | |
| --- | --- | --- | --- | --- | --- |
| Donor number | Optical density | Number of antigen molecules (in millions) per µl of blood | Optical density | Number of antigen molecules (in millions) per µl of blood | Molar ratio CD4/ CD8 |
| 12 | 0.73 | 28 | 0.85 | 46 | 0.61 |
| 13 | 0.51 | 18 | 0.66 | 30 | 0.60 |
| 14 | 0.65 | 24 | 1.06 | 76 | 0.31 |
| 15 | 0.92 | 42 | 0.87 | 48 | 0.87 |
| 16 | 0.77 | 31 | 0.98 | 63 | 0.49 |
| 17 | 0.68 | 25 | 1.01 | 67 | 0.37 |
| 18 | 0.85 | 36 | 0.96 | 61 | 0.59 |
| 19 | 0.91 | 41 | 0.90 | 52 | 0.79 |
| 20 | 1.00 | 50 | 1.02 | 69 | 0.72 |

EXAMPLE 2

Enzyme immunometric assay of the molecular concentration of the C-D4 and CD8 antigens in samples of human blood, in which the antibodies are labeled with alkaline phosphatase.

This determination is carried out in the same way as that of Example 1. The monoclonal antibody-alkaline phosphatase conjugate is prepared according to the method indicated by Boehringer Mannheim—Biochemica (ref. 567 744). After the cells to be determined have been incubated for one hour with this conjugate, the fixed enzyme is developed by the addition of a solution containing 1 mg/ml of paranitrophenyl phosphate in a buffer containing 1.2% of diethanolamine in distilled water, adjusted to pH 9.8 with a dilute solution of hydrochloric acid. After 2 hours at 37° C., the optical density is measured on a spectrophotometer at 405 nm.

The results are calculated and expressed as in Example 1.

EXAMPLE 3

Radioimmunometric assay of the molecular concentration of the CD4 and CD8 antigens in samples of human blood, in which the antibodies are labeled with iodine 125

The antibody labeled with iodine 125 is prepared according to the technique described by F. C. Greenwood, V. M. Hunter et al., Biochem. J., 1963, 89, 114.

50 µg of anti-CD4 or anti-CD8 monoclonal antibody contained in 50 µl of phosphate buffered saline of pH 7.2 are mixed with 37 MBq of iodine 125 in the form of sodium iodide and 30 µl of a solution containing 0.33 mg of chloramine T per ml in a phosphate buffered saline. After 1 minute of shaking, the reaction for labeling the monoclonal antibody is stopped by the addition of 100 µl of a solution containing 2.5 mg/ml of sodium metabisulfite. The solution prepared in this way is passed through a PD 10 column (Pharmacia-Sephadex G25M) and the fraction containing the radiolabeled antibody is recovered in the effluent. The determination is carried out by introducing into 4 microwells a volume of 100 µl of cell suspension containing mononucleate human blood cells prepared as in Example 1. 100 µl of dilute solution of radioactive antibody in a PBS buffer containing 5% of BSA are then deposited so as to introduce 150 000 cpm into each well; 2 microwells are each filled with 100 µl of the solution of the anti-CD4-$^{125}$I conjugate and 2 microwells are each filled with 100 µl of the solution of the anti-CD8-$^{125}$I conjugate. The fixation of the cells is improved by centrifugation of the plate for 3 minutes at 150×g after incubation for 1 hour at room temperature. The microwells are emptied by turning the plate over. The microwells are washed 4 times with 200 µl of PBS per well. 75 µl of 1 M sodium hydroxide solution are then introduced into each well. After 10 minutes, the contents of each well are recovered with an absorbent buffer before the radioactivity is counted in a W counter (LKB multiwell counter).

The results are calculated and expressed as in Example 1, the optical density values being replaced with the count results in dpm.

EXAMPLE 4

Checking the validity of the method

On 20 samples of human blood, the CD4 and CD8 antigens of the human T cells were measured by following the peroxidase immunometric assay method described in Example 1. The ratio of the number of positive T4 cells to the number of positive T8 cells was also determined on the same blood samples using the conventional cytological counting technique (W. W. ERBFR et al., Lancet, 1984, (8385), 1042–1045).

The correlation coefficient r between the ratio CD4/CD8 obtained by enzyme immunometric assay and the ratio T4/T8 obtained by cytological counting is 0.72.

Likewise, on 7 other samples of human blood, the ratio CD4/CD8 determined by the radioinmunometric assay method using labeling with iodine 125 by the process of the present invention was compared with the cell ratio T4/T8 determined by cell counting. The correlation coefficient r is 0.87.

In both cases, the correlation coefficients obtained show that, despite a satisfactory overall agreement between the results of the 2 techniques, the information provided by the 2 ratios is not equivalent; this is obvious since the determination of antigens according to the invention allows not only for the number of positive cells, as is the case for the cytological method, but also for the density of the antigen in question on the positive cells of each sample. The information given by the technique described in the present invention is therefore more complete than that given by the conventional reference technique (W. W. ERBFR et al., Lancet, 1984, (8385), 1042–1045).

EXAMPLE 5

Enzyme immunometric assay of the molecular concentration of the CD4 and CD8 antigens of the T lymphocytes in samples of human blood, in which the antibodies are labeled with peroxidase The purpose of this Example is to show that the time required for the determination can be reduced, relative to the conditions described in Example 1, by modifying on the one hand the cell separation process and on the other hand the incubation time required by the step for immunocapture and labeling of the cells.

A) Influence of the Process for the Separation of Cells from Whole Blood a) Technique involving brief centrifugation:

0.5 ml is taken from the blood sample to be determined and mixed with 1.5 ml of phosphate buffered saline. 1.5 ml of Ficoll-Paque, marketed by Pharmacia, are introduced into a 5 ml hemolysis tube and the blood sample, diluted in PBS, is deposited on the surface of the layer of Ficoll. Centrifugation at 900×g for 5 minutes at room temperature is followed by removal of the suspension ring containing the mononucleate cells in a volume of 0.5 ml. 1.5 ml of PBS are added to this sample.

b) Technique involving lysis of the erythrocytes:

Another rapid method for the separation of cells from blood is to use a buffer which Lyzes the erythrocytes. The lysis buffer, used by way of a non-limiting example, has the following composition:
ammonium chloride: 8.29 g
potassium bicarbonate: 1 g
disodium salt of ethylenediaminetetraacetic acid: 0.0307 g per liter of distilled water, the pH being adjusted to 7.3.

5 ml of lysis buffer are mixed with 0.250 ml of blood. After 10 minutes of shaking, the mixture is centrifuged at 600×g for 10 minutes. The cell residue formed is taken up in 1 ml of PBS buffer.

By subsequent determination of the CD4 and CD8 antigens under the conditions of Example 1, and by comparison with the reference protocol described in Example 1 for isolation of the mononucleate cells from blood, it was verified that both these variants of the method for the separation of the mononucleate cells from whole blood did indeed enable all the lymphocytes to be collected from the blood samples examined.

B) Influence of the Incubation Time for Immunocapture and Labeling of the Cells

In order to check whether the period of 1 hour used in Example 1 might be reduced in order to accelerate the determination, the results obtained for identical samples each containing 20 000 mononucleate cells per well were compared when the time allowed for capture and labeling of the cells was varied from 10 minutes to 1 hour. The results obtained are shown in Table 2, all other operating conditions being the same as in Example 1.

TABLE 2

| Incubation time (minutes) | Optical density | | | |
|---|---|---|---|---|
| | CD4 antigen | | CD8 antigen | |
| | Test | Blank* | Test | Blank* |
| 10 | 0.322 | 0.037 | 0.329 | 0.023 |
| 20 | 0.438 | 0.049 | 0.401 | 0.025 |
| 30 | 0.620 | 0.055 | 0.498 | 0.027 |

*These optical density values correspond to the reagent blank obtained in the absenced of cells with either the conjugate or the substrate being omitted are not greater than the values indicated.

These results show that:

The non-specific signal (reagent blank) always remains at low values which become lower as the time for which the conjugate is present becomes shorter.

After 10 minutes of contact, the specific signal reaches a value which can be processed analytically with precision and reproducibility. This indicates that it is possible, relative to the conditions of Example 1, significantly to reduce the time taken to carry out the determination without a substantial loss of precision in the results.

In practice, and if the time savings which can be achieved in the preparation of the blood sample and in immunocapture are added together, the kit and the process of the invention make it possible to determine the CD4 and CD8 antigens (by way of non-limiting examples) of samples of whole blood, at a rate of 10 or 20 samples per plate of 96 wells, in a total time (taken from reception of the samples in the laboratory) of no more than 1 hour. This level of productivity is greater than that of all the alternate techniques known to date.

EXAMPLE 6

Immunometric assay of the molecular concentration of the CD5 antigens of the human T lymphocytes in samples of human blood, in which the antibody is labeled with acetylcholinesterase A) Preparation of the Assay Kit a) Solid support A microtiter plate prepared in the manner described in Example 1 is used.

b) Monoclonal antibody-acetylcholinesterase conjugate

The acetylcholinesterase of Electrophorus electricus is used, which is obtained by the technique described in French Patent no. 2 550 799.

This enzyme is coupled to the anti-CD5 antibody called ST1 and marketed by BIOSYS. Coupling is carried out in accordance with the process described by YOSHITAKE et al., Eur. J. Biochem., 101 (1979), 395–399.

c) Developing reagent

This reagent comprises both the substrate for the enzyme (acetylthiocholine) and Fllman's reagent and has the following composition:
acetylthiocholine $7.5 \times 10^{-4}$ M
5,5'-dithio-2-nitrobenzoic acid (DTNB) $5 \times 10^{-4}$ M in 1 M sodium phosphate buffer of pH 7.4.

This solution is diluted 100-fold in distilled water before use.

B) Immunometric Assay Process a) The mononucleate cells are separated off using the method described in Example 1.

b) Incubation of the cells for the immunocapture and labeling step takes 20 minutes, as in Example 5.

c) Development of the fixed enzyme and measurement.

100 µl of developing reagent are added to each microwell. The absorbance is measured at 412 nm after 45 minutes of incubation.

The measured optical densities for samples containing known numbers of T cells are given in Table 3. Under these experimental conditions, the reagent blank is particularly weak and corresponds to an optical density of 0.002 to 0.003.

TABLE 3

| | Number of T lymphocytes introduced into each well and number of molecules of CD5 antigen present in each well, in millions | | | | | |
|---|---|---|---|---|---|---|
| | 540 (32) | 1 080 (65) | 2 160 (130) | 4 320 (260) | 8 640 (520) | 17 280 (1040) |
| Optical density | 0.030 | 0.060 | 0.138 | 0.260 | 0.470 | 0.850 |

These results reveal the extreme sensitivity of the technique developed in this way. In fact, the optical density of 0.030 obtained in the well containing 540 T lymphocytes (i.e. 32 million molecules of CD5 antigen), which is measurable with precision and equal to 10 times the background, corresponds to about $5 \cdot 10^{-17}$ mol of CD5 antigen per assay well. Such sensitivity is of the same order as that of the best immunoassays known, which use the most sensitive radioactive tracers.

EXAMPLE 7

Determination of different antigens expressed on activated human T lymphocytes

Activation of the T lymphocytes is a physiological process which takes place prematurely every time the immune system is stressed, for example as in infectious pathologies, organ transplantations and certain dysimmune diseases. This natural process is also commonly used in vitro in the laboratory in tests such as, in particular, mixed lymphocytic reactions or lymphoblastic transformation tests. In the latter case, polyclonal activation is obtained by the use of agents such as phytohemagglutinin (PHA), concanavalin A or other lectins. Activation of the T lymphocytes is accompanied by a considerable increase in the expression of several membrane markers, and especially the CD25 antigen (receptor of interleukin 2) or the CD2 antigen. These antigens therefore constitute excellent markers of the activation state and their determination is of great interest both in clinical biology and for laboratory work, as indicated above, the use of radioactive reagents being avoided in all cases.

These antigens are measured using the method described in Example 1 with the specifications detailed in Table 4.

TABLE 4

Measurement of the surface antigens of activated T lymphocytes

| Antigen measured | Antibody used for immunocapture, marketed by | Antibody labeled with peroxidase, marketed by | |
|---|---|---|---|
| CD2 | ST1 BIOSYS | ST11 | BIOSYS |
| CD25 | ST11 BIOSYS | IOT14 | IMMUNOTECH |

The optical density values measured at 450 nm for the $25 \cdot 10^3$ mononucleate cells used are reported in Table 5 below and show the comparison between the cells without stimulation with PHA and the same cells after 3 days of stimulation.

TABLE 5

| | Optical density | | |
|---|---|---|---|
| Antigen | Non-activated cells | Cells activated for 3 days | Reagent blank |
| CD25 | 0.064 | 0.529 | 0.044 |
| CD2 | 0.129 | 0.768 | 0.027 |

These results show that the specific signals of the 2 antigens examined increase considerably when activation takes place.

EXAMPLE 8

Determination of the CD22 and HLA-Dr (or class II HLA) antigens present on B lymphocytes The present Example describes the determination of these antigens on cells of the RAJI line, which is a human B lymphoid line described by PULVERTAFT in J. Clin. Pathol., 1965, 18, 261–274.

For immunocapture of the cells, either the S-class II antibody (BIOSYS) for determination of the CD22 antigens, or the SB4 antibody (BIOSYS) for determination of the class II HLA (or HLA-Dr) antigens, was adsorbed in the assay wells as indicated in Example 1.

a) Determination of the CD22 antigen:

The SB22 antibody (BIOSYS) was labeled with iodine 125 by the method described in Example 3. The CD22 antigens are determined in the manner indicated in Example 3 for the CD4 and CD8 antigens, the following being introduced successively into the microwells: $5 \cdot 10^4$ cells of the RAJI line and then $10^5$ cpm of the labeled SB22 antibody. After a period of one hour at 4° C., the microwells are emptied by turning the plate over and then washed 4 times with 200 µl of PBS per well for each wash. The radioactivity fixed to the cells is recovered and counted as in Example 3. This gives a count of 760 dpm for the well containing $5 \times 10^4$ RAJI cells with a reagent blank (without cells) of 50 dpm.

b) Determination of the HLA-Dr antigen:

$10^5$ cells are introduced into the wells, followed by the conjugate of S-class II antibody labeled with peroxidase by the process described in Example 1. The determination is carried out according to the same protocol as in Example 1. This gives an optical density of 1.840 and a reagent blank, without cells, of 0.105.

EXAMPLE 9

Use of the process according to the invention for the measurement of antigens carried by the T lymphocytes and B lymphocytes of human blood A) Preparation of the Plates The plates used are microtiter plates prepared as in Example 1 except that monoclonal antibodies capable of fixing at least all the T lymphocytes (S-class I from BIOSYS) and the 9 lymphocytes (S-class II from BIOSYS), each one being used at a concentration of 5 µg/ml, are simultaneously adsorbed in each well of the microplate.

B) Immunometric Assay

The mononucleate cells are separated from the whole blood with the aid of Ficoll under the conditions of Example 1 or Example 5, after which 80 000 mononucleate cells in 75 Pt of PBS buffer are introduced into each well. The T lymphocytes are measured in some of the wells with the ST11 (anti-CD2) antibody from BIOSYS; the B lymphocytes are measured in other wells with the SB3 (anti-CD37) antibody from BIOSYS, which recognizes all the peripheral B lymphocytes. These antibodies are first coupled to peroxidase according to the protocol described in Example 1. The actual determination is carried out as in Example 1.

C) Results

The absolute numbers of T lymphocytes and B lymphocytes contained in the sample examined are determined by reference to calibration curves established by carrying out an identical treatment on mononucleate cells in which the T and B lymphocytes have been counted by a reference technique.

Alternately, by means of appropriate standards, the results can also be expressed as molar concentrations of the CD2 and CD37 antigens in the sample examined.

EXAMPLE 10

Determination of the GpIIb-IIIa and CD9 antigens of human blood platelets

This determination is carried out according to Example 3 using monoclonal antibodies radiolabeled with iodine 125.

The platelets are isolated from human blood by centrifugation in the presence of PLASMION perfusion liquid (Laboratoire R. Bellon). 5 ml of blood plus ml of phosphate buffered saline (PBS) and 10 ml of PLASMION are mixed in a tube. The tube is then centrifuged for 10 minutes at 1500 rpm. The platelets which have collected in the supernatant are removed by suction with a pipette. They are washed once in PBS by mixing 1 volume of the platelet suspension with 10 ml of PBS, and then centrifuged for 10 minutes at 1000×g. Finally, the platelet residue is collected and resuspended n PBS (2 ml). The platelets are counted and their concentration adjusted to 2.5 million/ml of PBS.

The GpIIb-IIIa antigen is determined by immuno-capture of the platelets by the monoclonal antibody IOB2 (Immunotech) and labeling of the GpIIb-IIIa antigen with the monoclonal antibody P2 (Immunotech).

The CD9 antigen is determined by immunocapture by the monoclonal antibody P2 and labeling with the monoclonal antibody IOB2. The number of dpm is measured for a sample comprising 200 000 platelets.

The results are shown in Table 6.

TABLE 6

| Antigen measured | Sample measured (dpm) | Control without cells (dpm) |
|---|---|---|
| CD9 | 1927 | 113 |
| GpIIb-IIIa | 2891 | 238 |

EXAMPLE 11

Determination of the CD15 antigens carried by human granulocytes

The CD15 antigen is a good specific marker of human granulocytes (also called polynuclear leukocytes). These cells can be evaluated by means of this antigen, in the blood, in the same way as for any other leukocytic subpopulation. This evaluation is also useful for assessing the presence of granulocytes in the urine, for example in cases of urinary infections such as cystitis or pyelonephritis. In the present Example, the determination was carried out on granulocytes originating from whole blood and separated off as indicated below.

The granulocytes, as well as some of the mononucleate cells, are separated from the erythrocytes by a process analogous to that described in Example 10 for the platelets, except that the tube containing the cells is left to stand for 45 minutes at room temperature and the suspension of leukocytes is recovered in a volume of 500 μl taken from the surface of the liquid.

The granulocytes are immobilized in the wells with a monoclonal antibody specific for the CD45 antigen present on the cell membrane of all the leukocytes: the anti-LCA antibody (BIOSYS) is used and is adsorbed in the microwells of the titer plate, as indicated in Example 1.

The determination is carried out using the anti-CD15 monoclonal antibody SMY-15a (BIOSYS) labeled with peroxidase by the technique of Example 1.

Thus, with a total of 12 500 cells introduced into each well, the specific signal of the CD15 antigen of the granulocytes is 0.616 after correction of the crude optical density for a reagent blank of 0.100, obtained in the presence of the cells and in the absence of enzyme conjugate and due to the endogenous peroxidases of the granulocytes.

EXAMPLE 12

Evaluation of the phenotype of a leukemia by the enzyme immunometric assay process.

The phenotyping of the tumoral cells of a leukemia patient is a systematic diagnostic examination performed in order to characterize the type and origin of the patient's leukemia cells (T, B, granulocytes, myeloblasts, etc.). This examination is conventionally performed by the immunofluorescence technique by using a set of monoclonal antibodies and by observing and counting the positive cells under a microscope. Flux cytometry is also used to analyze the labeling of the cells.

The use of monoclonal antibodies in the process according to the invention makes it possible to identify the major clinically important groups of acute or chronic leukemias and also provides quantitative information on the relative densities of the different antigens examined.

6 peroxidase-coupled monoclonal antibodies specific for antigens present on the leukemia cells were prepared in this Example:
ST1 and ST11 (BIOSYS): anti-CD5 and anti-CD2
SB3 (BIOSYS): anti-CD37
S-CALLA (SANOFI): anti-CALLA (or anti-CD10)
S-class II (BIOSYS): anti-HLA-Dr (or anti-class II HLA)
SMY15 (BIOSYS): anti-CD15

The microtiter plate is prepared by the prior adsorption of a mixture of anti-CD45 monoclonal antibodies (S-LCA, BIOSYS) and anti-class I HLA monoclonal antibodies (S-class I, BIOSYS).

The phenotype of chronic lymphoid leukemia B (CLL-B) was evaluated using the 6 monoclonal antibodies selected above; it was also characterized by the conventional method.

The optical densities measured at 492 nm are reported in Table 7 below for a total of 80 000 mononucleate cells introduced into each well or for the control wells without cells. For the control well containing the cells but no peroxidase-labeled antibody, the optical density is 0.110.

TABLE 7

| Monoclonal antibody and corresponding antigen | Optical density | |
|---|---|---|
| | Sample with cells | Control without cells |
| ST11 (CD2) | 0.270 | 0.030 |
| ST1 (CD5) | 1.350 | 0.014 |
| SB3 (CD37) | 0.850 | 0.005 |
| S-class II (HLA-Dr) | 1.640 | 0.010 |
| SMY15 (CD15) | 0.235 | 0.007 |
| CALLA (CD10) | 0.160 | 0.002 |

Thus the leukemia cells studied carry an abundance of the CD5, CD37 and class II HLA antigens, but they carry no CD15, CALLA and CD2 antigens, or very few, which is characteristic of a CLL-B.

EXAMPLE 13

Determination of antigens associated with cancers of the urinary system.

The kits and processes of the present invention are very particularly suitable for the detection of tumoral cells, especially in the case of tumors of the urinary system, and are applicable to the mass screening of high-risk populations, for example workers in the chemical industry of other very exposed groups.

The present Example shows the application of the invention to the determination of an antigen associated with cancer of the bladder, on cells of the RT4 line originating from a human urinary papilloma (C. C. Rigby and L. M. Franks, Brit. J. Cancer, 1970, 24, 746–754).

The plates intended for immunocapture of the cells are prepared as in Example 1, the monoclonal antibody S-class I (BIOSYS), which recognizes a class I HLA antigen and is capable of retaining all the epithelial cells, being adsorbed in the wells.

The labeled conjugates are obtained by the processes of Example 1 (for enzyme labeling) or Example 3 (for radioisotopic labeling) with the monoclonal antibody 12F6 (SANOFI), which recognizes an antigen associated with cancer of the bladder.

For the determination, 75 µl of the cell suspension are distributed into 4 microwells (i.e. 50·10³ cells per well). The conjugate of the monoclonal antibody 12F6 (SANOFI) coupled with peroxidase is introduced into 2 wells and the antibody 12F6 labeled with iodine 125 is introduced into the other 2 wells (100 000 cpm/well). The results obtained by applying the enzyme immunometric assay process or the radioimmuno-metric assay process are reported in Table 8.

TABLE 8

| Labeled monoclonal antibody | Optical density (at 492 nm) or cpm | | Ratio of positive signal to non-specific signal |
|---|---|---|---|
| | Sample to be determined | Control | |
| 12F6-peroxidase | 0.782 | 0.078 | 10.0 |
| 12F6-iodine 125 | 1612 | 350 | 4.6 |

EXAMPLE 14

Enzyme immunometric assay of a membrane antigen of the yeast *Candida albicans*

The *Candida albicans* cells (serotype 17) originate from the Institut Pasteur collection, Paris. The yeasts are cultivated for 18 hours in the usual way on a solid synthetic medium. The cells are counted and a cell suspension containing $10^5$ cells per ml of PBS buffer solution is prepared.

The anti-*Candida albicans* monoclonal antibodies used were prepared by lymphocytic hybridization as described in the thesis of T. Chardes, Faculty of Pharmacy, University of Montpellier I, 1988.

The antibody CA4 is used for immunocapture while the antibody CA12 labeled with peroxidase is used for the determination under the conditions of Example 1.

The optical density values measured at 492 nm for the well containing the introduced cells and for the control sample without cells are 1.025 and 0.080 respectively.

EXAMPLE 15

Enzyme immunometric assay carried out on magnetic beads: determination of the CD5 antigen of human T lymphocytes with a conjugate of antibody labeled with acetylcholinesterase and a particulate support formed of magnetic beads.

The support used to capture the cells consists of magnetic beads known as DYNABEADS. The beads, marketed by BIOSYS under ref. DYN1110, carry on their surface an anti-CD2 antibody capable of fixing all the T lymphocytes in the sample examined. These beads are treated again with a solution of anti-CD2 antibody before use in order to improve the performance characteristics of the determination.

This is done by mixing 10 µl of the suspension of beads with 1 µl of antibody solution containing 25 µg/ml of PBS buffer, for 1 hour, with gentle shaking. The beads are subsequently washed 4 times with PBS buffer and then kept in 4 ml of PBS buffer.

For the determination, 200 µl of the suspension of beads and 80 µl of a suspension of mononucleate cells separated from whole blood with the aid of Ficoll-Paque (PHARMACIA) are introduced successively into a 5 ml tube and 280 µl of a conjugate of antibody ST1 labeled with acetylcholinesterase, identical to that used in Example 6, are then added.

After one hour of gentle shaking, the beads are separated off by means of a magnet and the cells fixed to the beads are washed with PBS buffer (5 washes).

The acetylcholinesterase fixed to the cells is developed in the same way as in Example 6. The optical density signal obtained is 0.168 in the presence of the labeled cells; the blank obtained without the cells gives a value of 0.062.

EXAMPLE 16

Assay of CD 15 Antigen of Polynuclear Leucocytes of the Human Blood with Using of Magnetic Beads CD 15 antigen is a specific label of human granulocytes (also named polynuclear leucocytes). The determination of these cells by means of this antigen may be carried out in the blood, as for each other leucocyte sub-population. It is also useful, for example in the case of urinary infections, such as cystitis or pyelonephritis. In the present example, the determination was directly carried out on the complete blood.

The assay of CD 15 antigen of polynuclear leucocytes according to the invention process was effected in one step comprising the immunocapture of the polynuclear leucocytes by a monoclonal anti-CD45 antibody fixed on a particulate magnetic support and the simultaneous labeling of the CD 15 antigens by the monoclonal anti-CD15 antibody (reference SMY-15a BIOSYS, Compiegne France) labeled by peroxidaxe.

Magnetic beads which allow the specific capture of the cells were used as support. The beads named DYN -11001 (DYNABEADS) bear on their surface the anti-mouse immunoglobulin antibodies. The beads were treated before use with a solution of monoclonal anti-CD45 antibody (called S-LCA1 and marketed by BIOSYS, France) during 12 hours at 4° C. For this purpose, 25 µl of the bead suspension were mixed with 0.5 ml of the antibody solution at 100 µg/ml in PBS buffer. The beads were thereafter washed three times with PBS buffer and then saturated during 12 hours at 4° C. by a 0.3% solution of bovine serum albumine (BSA). The ready-to-use beads were preserved at 4° C.

The assay of the CD 15 antigens was carried out in 5 ml hemolysis tube; 300 µl of phosphate buffered saline (PBS) containing the SMY-15a antibody labeled with peroxidase were introduced into the tube, at the concentration of 2.5 µg of antibody per ml of buffer; then 25 µl of the bead suspension and 100 µl of the complete blood taken on lithium heparinate (tube VACUTAINER reference 606484) were added. After five minutes of mild stirring, the beads were separated from the blood by means of a magnet and the cells fixed on the beads were washed with PBS (five washings).

After a last washing, 100 µl of the developing reagent were introduced into the tube. The developing reagent is obtained by the following manner:

A 0.1 M citrate buffer is prepared by dissolving citric acid monohydrate in water at a concentration of 2.1% and adjusting the pH to 5 by the addition of 7 N sodium hydroxide solution. 30 mg of orthophenylenediamine dihydrochloride are then added to 20 ml of the citrate buffer obtained, after which 40 µl of hydrogen peroxide (substrate for the enzyme) are added at the last moment.

After incubation of the reagent in the tube during 10 minutes, the optical density is measured on a spectrophotometer at 450 nm.

The optical densities obtained for one trial are given thereafter:

|  | measured sample | |
|---|---|---|
|  | control samples | Beads + Blood |
|  | Beads | Beads + Blood + reagent | + anti-CD 15 antibody labeled with peroxidase +reagent |
| Optical densities | 0.012 | 0.071 | 0.894 |

The low signal observed for the control sample containing the blood and the reagent without the immunoenzymatic conjugate results from the development of endogen peroxidases of the granulocytes by this reagent.

According to the process disclosed in this sample, the assay was directly carried out on the blood sample, without previous separation of the cell population to be assayed.

On the other hand, the incubation period was only five minutes. Thus, by using magnetic beads as solid support, all the assaying steps are particularly simple and rapid.

What is claimed is:

1. A kit for quantitative determination of specific antigens of T and B lymphocytic subpopulations, which consists essentially of:
   a) a plurality of solid supports to which are bound one or more monoclonal capture antibodies that specifically bind to surface antigens, other than the antigen to be determined, characteristic of a T or B lymphocytic subpopulation;
   b) a solution of a monoclonal probe antibody that specifically binds to a surface antigen to be determined of the T or B lymphocytic subpopulation, the monoclonal probe antibody being labeled with a radioisotope label or an enzyme label; and
   c) a series of reference samples containing appropriate cells bearing both the antigens recognized by said capture antibodies and known amounts of the surface antigen to be determined,
   wherein each solid support is a well in a multiwell plate in which one or more monoclonal capture antibodies specific for surface antigens of said T or B lymphocytic subpopulation have been fixed, and wherein the kit comprises a plurality of monoclonal probe antibody containing solutions each containing a different monoclonal probe antibody specific for a surface antigen of said T or B lymphocytic subpopulation.

2. The kit according to claim 1, for the determination of specific antigens of T4 and T8 lymphocytic subpopulations.

3. A process for quantitative immunometric determination of specific antigens of T and B lymphocytic subpopulations, which consists essentially of:
   (1) contacting a sample containing a T or B lymphocytic subpopulation carrying a surface antigen to be determined with a solid support to which is bound one or more monoclonal capture antibodies that specifically bind to surface antigens, other than the antigen to be determined, characteristic of said T or B lymphocytic subpopulation, and concurrently, with at least one monoclonal probe antibody which specifically binds to said surface antigen to be determined, the monoclonal probe antibody being labeled with a radioisotope label or an enzyme label;
   (2) observing an incubation period, during which intact cells in said T or B lymphocytic subpopulation are captured by said capture antibodies and immobilized on said multiwell plate, and the surface antigen to be determined on said intact cells binds said labeled probe antibody;
   (3) washing the plate to remove the nonimmobilized cells, the excess probe antibody and other unbound sample constituents;
   (4) counting the amount of radioactivity on said plate, or adding a substrate for said enzyme label and measuring a detectable signal correlating with the amount of said enzyme on said plate; and
   (5) comparing the counted radioactivity or the measured signal with a calibration curve to determine the amount of said surface antigen on the desired T or B lymphocytic subpopulation in said sample,
   wherein said calibration curve is prepared using a series of reference samples containing appropriate cells bearing both the antigen or antigens recognized by said capture antibodies and known amounts of the surface antigen to be determined and wherein said process comprises immobilizing a cell population comprising a T or B lymphocytic subpopulation carrying the antigen to be determined on a multiwell plate with one or more monoclonal capture antibodies specific for surface antigens of this population, and, in the same step, directly labeling cell subpopulations making up the said population, wherein different wells are contacted with different solutions and wherein each solution contains a probe monoclonal antibody specific for a surface antigen of one of the cell subpopulation to be determined.

4. The process according to claim 3, for the determination of specific antigens of T4 and T8 lymphocytic subpopulations.

5. A kit for quantitative determination of a surface antigen on a cell population or subpopulation, which consists essentially of:
   a) a plurality of solid supports to which are bound one or more monoclonal capture antibodies that specifically bind to surface antigens, other than the antigen to be determined, characteristic of a desired cell population or subpopulation that excludes bacterial cells and blood platelets;
   b) a solution of a monoclonal probe antibody that specifically binds to a surface antigen to be determined of the desired cell population or subpopulation, the monoclonal probe antibody being labeled with a radioisotope label or an enzyme label; and
   c) a series of reference samples containing appropriate cells bearing both the antigens recognized by said capture antibodies and known amounts of the surface antigen to be determined,
   wherein said capture and probe antibodies specifically bind to one or more surface antigens of T lymphocytes.

6. The kit according to claim 5, wherein said surface antigens are one or both of the CD4 or CD8 antigen on one or both of T4 lymphocytes and T8 lymphocytes.

7. A process for quantitative immunometric determination of a surface antigen on a cell population or subpopulation, which consists essentially of:

(1) contacting a sample containing a desired cell population or subpopulation carrying a surface antigen to be determined, said population or subpopulation excluding bacterial cells and blood platelets, with a solid support to which is bound one or more monoclonal capture antibodies that specifically bind to surface antigens, other than the antigen to be determined, characteristic of said desired cell population or subpopulation, and, concurrently, with at least one monoclonal probe antibody which specifically binds to said surface antigen to be determined, the monoclonal probe antibody being labeled with a radioisotope label or an enzyme label;

(2) observing an incubation period, during which intact cells in said desired cell population or subpopulation are captured by said capture antibodies and immobilized on said solid support, and the surface antigen to be determined on said intact cells binds said labeled probe antibody;

(3) washing the support to remove the nonimmobilized cells, the excess probe antibody and other unbound sample constituents;

(4) counting the amount of radioactivity on said solid support, or adding a substrate for said enzyme label and measuring a detectable signal correlating with the amount of said enzyme on said solid support; and (5) comparing the counted radioactivity or the measured signal with a calibration curve to determine the amount of said surface antigen on the desired cell population or subpopulation in said sample, wherein said calibration curve is prepared using a series of reference samples containing appropriate cells bearing both the antigen or antigens recognized by said capture antibodies and known amounts of the surface antigen to be determined, wherein said capture and probe antibodies specifically bind to antigens present on human T4 lymphocytes carrying the CD4 marker.

8. A process for quantitative immunometric determination of a surface antigen on a cell population or subpopulation, which consists essentially of:

(1) contacting a sample containing a desired cell population or subpopulation carrying a surface antigen to be determined, said population or subpopulation excluding bacterial cells and blood platelets, with a solid support to which is bound one or more monoclonal capture antibodies that specifically bind to surface antigens, other than the antigen to be determined, characteristic of said desired cell population or subpopulation, and, concurrently, with at least one monoclonal probe antibody which specifically binds to said surface antigen to be determined, the monoclonal probe antibody being labeled with a radioisotope label or an enzyme label;

(2) observing an incubation period, during which intact cells in said desired cell population or subpopulation are captured by said capture antibodies and immobilized on said solid support, and the surface antigen to be determined on said intact cells binds said labeled probe antibody;

(3) washing the support to remove the nonimmobilized cells, the excess probe antibody and other unbound sample constituents;

(4) counting the amount of radioactivity on said solid support, or adding a substrate for said enzyme label and measuring a detectable signal correlating with the amount of said enzyme on said solid support; and (5) comparing the counted radioactivity or the measured signal with a calibration curve to determine the amount of said surface antigen on the desired cell population or subpopulation in said sample, wherein said calibration curve is prepared using a series of reference samples containing appropriate cells bearing both the antigen or antigens recognized by said capture antibodies and known amounts of the surface antigen to be determined, wherein said capture and probe antibodies specifically bind to antigens present on human T8 lymphocytes carrying the CD8 marker.

* * * * *